United States Patent [19]

Saez et al.

[11] Patent Number: 4,925,449
[45] Date of Patent: May 15, 1990

[54] MANUALLY DRIVEN SYRINGE

[75] Inventors: Carlos A. Saez, Irvine; Robert P. Cooper, Yorba Linda, both of Calif.

[73] Assignee: Applied Vascular Devices, Laguna Hills, Calif.

[21] Appl. No.: 227,557

[22] Filed: Aug. 2, 1988

Related U.S. Application Data

[63] Continuation-in-part of Ser. No. 141,989, Jan. 11, 1988, abandoned.

[51] Int. Cl.$^5$ .............................................. A61M 5/00
[52] U.S. Cl. ...................... 604/227; 604/218; 604/209; 222/386
[58] Field of Search .............. 604/187, 207–209, 604/218, 220, 227, 97–99; 222/386

[56]  References Cited

U.S. PATENT DOCUMENTS

| 201,443 | 3/1878 | Parker | 604/209 |
|---|---|---|---|
| 794,190 | 7/1905 | Schneyder | 604/227 |
| 1,325,699 | 12/1919 | Oesterhaus | 604/227 |
| 1,654,905 | 1/1928 | Voos | 604/227 |
| 2,420,102 | 5/1947 | Shuford | 604/227 |
| 2,632,445 | 3/1953 | Kas | 604/209 |
| 2,671,449 | 3/1954 | Dann | 604/227 |
| 2,882,901 | 4/1959 | DeVenezia | 604/227 |
| 3,043,304 | 7/1962 | Higgins | 604/227 |
| 3,306,290 | 2/1967 | Weltman | 604/227 |
| 4,340,051 | 7/1982 | Leibinsohn | 604/227 |

FOREIGN PATENT DOCUMENTS

| 0157260 | 12/1904 | Fed. Rep. of Germany | 604/227 |
|---|---|---|---|
| 1287742 | 1/1969 | Fed. Rep. of Germany | 604/202 |
| 6400092 | 11/1965 | Netherlands | 604/227 |

Primary Examiner—Stephen C. Pellegrino
Assistant Examiner—Ralph Lewis
Attorney, Agent, or Firm—Irell & Manella

[57]  ABSTRACT

A manually driven syringe for injecting fluids under high pressure is described that includes a barrel (12), a plunger (13) that is received within the barrel and extends rearwardly through an aperture (28) in the body (27) of a handle (14) which carries a pair of opposed finger grips (19, 22). The finger grips are located rearwardly of the barrel and laterally of the shaft (19) of the plunger, elongated so as to each accommodate two fingers, and angled rearwardly. This design minimizes the distance between (a) the inner edges of the grips and (b) the grips and the head of the extended plunger, thus making the syringe easier to grip in the palm of the hand and enabling the syringe to be gripped strongly between the fingers and the palm.

8 Claims, 2 Drawing Sheets

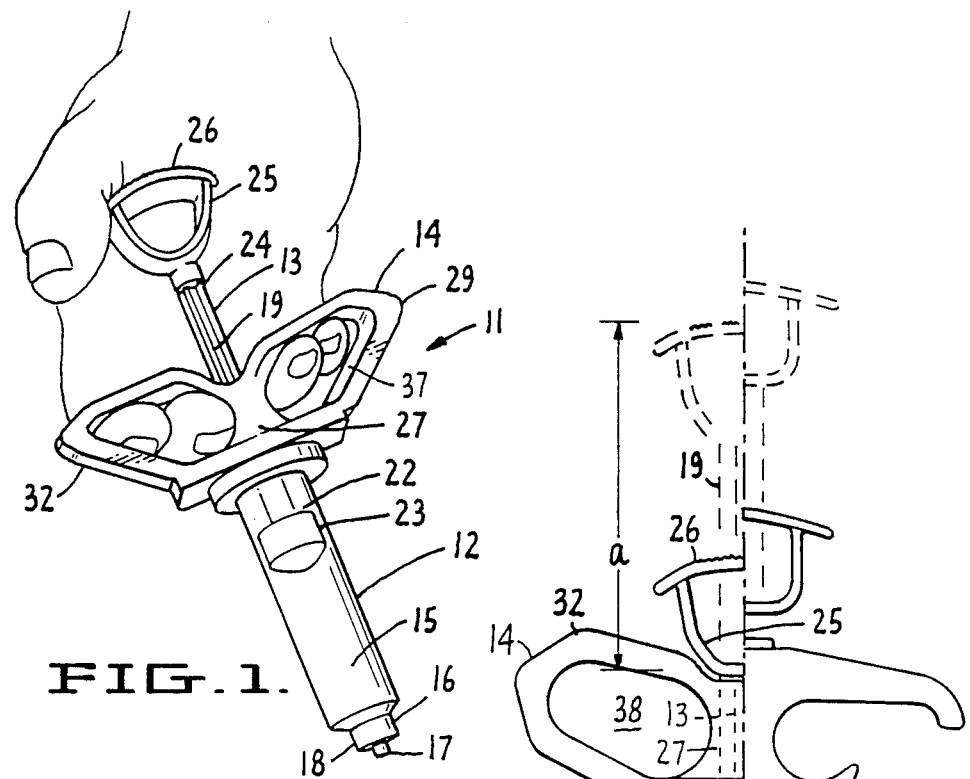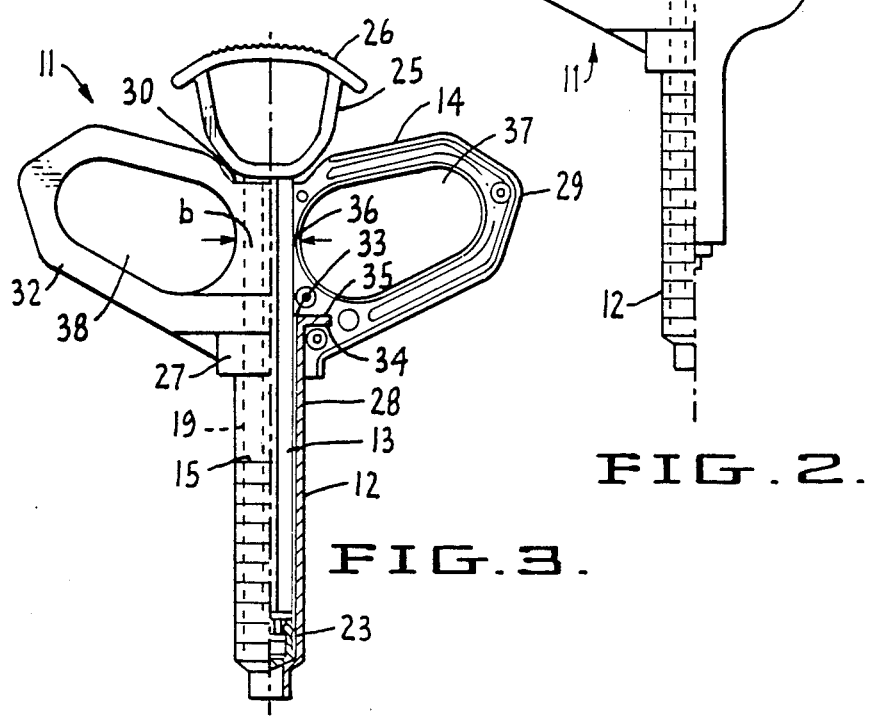

MANUALLY DRIVEN SYRINGE

CROSS-REFERENCE TO RELATED APPLICATION

This application is a continuation-in part of copending U.S. patent application Ser. No. 141,989 filed Jan. 11, 1988, now abandoned, the disclosure of which is hereby incorporated by reference.

DESCRIPTION

1. Technical Field

The invention relates to the manual injection of viscous solutions in medical or commercial applications. In medical applications, the invention is useful in injecting dye and medical solutions into patients or catheters In industrial applications, the device has numerous uses such as manual application of viscous adhesives in controlled amounts.

2. Background Art

Injection of radioactive "dye" solutions during diagnostic and therapeutic procedures is conducted millions of times every year. The purpose of the practice is to propel the radioactive solution into cavities of blood vessels of patients so that the details of the anatomy may be captured by radioimaging on film or screen.

Generally, radioimaging is done more frequently and elaborately during diagnostic procedures, where mapping of the anatomy is required for further evaluations. But dye injection is also needed during therapeutic procedures, such as angioplasty, in order to enable the physician to evaluate catheter location, condition of the lesion, nature of the stenosis, progress of the procedure, and effectiveness of the dilation.

During diagnostic or therapeutic procedures requiring dye injection, the dye must be injected under pressure to ensure the delivery of adequate amounts to the site. The dye solution, even when diluted to fifty or seventy-five percent concentrations, remains viscous and relatively hard to propel within the small lumens of catheters. In most diagnostic procedures, special high-pressure injection equipment is used.

High pressure injection during therapeutic procedures is typically done manually. The most common approach is the use of a hand-gripped syringe which is intended to enable the user to apply sufficient force to the plunger to inject the dye. These devices are used in coronary angioplasty procedures as well as many other vascular, urological and general surgical procedures. A commercial example of such a device is the ANGIOJECT syringe which is sold by ACS.

Key to the ability to muster enough force to inject the solution is the manner in which the device fits within the hand. The maximum grip power is achieved as the fingers of the user are brought to a closed-fist position. However, in order to achieve the preferred manner of applying the force to the syringe plunger, the distance between where the fingers grip the handle and the top of the extended plunger must be such that the head of the extended plunger fits within the palm of the average user. Most syringes in use that can accommodate five to twenty milliliters of solution have a stroke in excess of 7.5 cm, thus making the preferred grip of the device hard to achieve. Because of this, a majority of users have to revert to applying force to the plunger by placing the device between the bent fingers and the tip of the thumb, a position that is awkward and nonconducive to applying maximum force on the plunger.

Another difficulty with the present devices is the way the device has to fit between the third and fourth fingers of the hand. Ergonomically, the hand can muster higher gripping forces if the third and fourth fingers are close to each other than when these two fingers are spread apart. For instance, in the ANGIOJECT syringe, the spread of the two fingers is dictated by the diameter of the syringe barrel; the smallest spread thus becoming equivalent to that diameter.

In summary, the ideal device is one that is ergonomically designed to take advantage of the gripping power of the hand by having the extended plunger fit within the palm of the user's hand, and having a configuration that minimizes the spread between the third and fourth fingers.

Other requirements include light weight, column strength and comfortable fit. A 10 cc syringe will experience the equivalent of forty pounds of force or more during rapid injections. The plunger must have the necessary column strength to prevent buckling or deformation. The device should enjoy a comfortable fit within the palm and accommodate the fingers. Slightly sharp edges and uncomfortable contours become more so during the injection process.

Presently available syringes or injectors fall short of such requirements. This necessitates either the use of more elaborate, and thus more expensive, equipment, or the acceptance of less than optimal bolus injections, both options having obvious as well as subtle consequences.

Accordingly, a primary object of the invention is to provide a device that has a short distance between the location where fingers two, three, four and five grip the device and the external end of the plunger while the plunger is in the extended position, thus permitting the external end of the plunger to fit comfortably within the palm of the average user's hand.

It is another object to provide embodiments of the invention that have a very short distance between the third and forth fingers as the device is held.

It is still another object of the invention to provide an ergonomically designed device with optimal fit to accommodate comfort, ease of use and lightness.

SUMMARY OF THE INVENTION

The invention provides a novel manually driven syringe that has several novel features that enable one or more of the active objects to be achieved. These features are: (1) use of opposed finger grips that are elongated so as to comfortably accommodate two fingers and are angled rearwardly relative to the syringe barrel so that the distance between the fingers and the extended plunger head is lessened, (2) configuring the plunger head and handle portion of the syringe such that the head nests into the handle, (3) having the syringe barrel extend through only the front portion of the handle so that distance between the inner ends of the finger grips may be lessened and (4) having the plunger head be axially collapsible so that the distance between the fingers and the top of the plunger head is reduced. Syringes that include one or any combination of these features are intended to be within the scope of the invention.

Accordingly, one embodiment of the invention is a manually driven syringe comprising: (a) a barrel for housing a fluid to be injected having a front end and a rear end; (b) a plunger comprising a shaft that is received within the barrel and has a front end which carries a piston and a rear end which carries a head that is adapted to fit within the palm of the hand; and (c) a handle member having (i) a central body through which an axial aperture extends, said aperture having a front end into which the rear end of the barrel is received, and (ii) a pair of opposed finger grips that are elongated to each accommodate two fingers said finger grips extending outwardly from the central body of the rear section and being angled rearwardly relative thereto whereby the distance between the location on the grips where the second, third, fourth and fifth fingers are placed and the plunger head when the plunger is extended is lessened.

Another embodiment of the invention is a manually driven syringe comprising (a) a barrel for housing a fluid to be injected and having a front and a rear end; (b) a plunger comprising a shaft that is received in the barrel and has a front end which carries a piston and a rear end which carries a head that is adapted to fit within the palm of the hand; and (c) a handle member having (i) a central body through which an axial aperture extends, said aperture having a front section into which the rear end of the barrel is seated, and a rear section of smaller diameter than the front section and through which the shaft of the plunger extends, and (ii) a pair of opposed finger grips extending outwardly from the central body laterally of the rear section of the aperture, the distance between the inner ends of the finger grips being less than the diameter of the barrel.

Yet another embodiment of the invention is a manually driven syringe comprising (a) a barrel for housing a fluid to be injected having a front end and a rear end; (b) a plunger comprising a shaft that is received within the barrel and has a front end which carries a piston and a rear end which carries a head that is adapted to fit within the palm of the hand; and (c) a handle member having (i) a central body through which an axial aperture extends, said aperture having a front end into which the rear end of the barrel is received and a rear end that opens into a recess in the rear surface of the handle, and (ii) a pair of opposed finger grips that are elongated to each accommodate two fingers said finger grips extending outwardly from the central body wherein the front surface of the head is configured to nest within the recess in the handle when the plunger is depressed.

Still another embodiment of the invention is a manually driven syringe comprising (a) a barrel for housing a fluid to be injected having a front end and a rear end; (b) a plunger comprising a shaft that is received in the barrel and has a front end which carries a piston and a rear end which carries a head that is adapted to fit within the palm of the hand, said head being collapsible under pressure from an uncollapsed configuration in which the head forms an enclosed openinq that provides a thumb grip to a collapsed configuration in which the axial dimension of the head is diminished; and (c) a handle member having (i) a central body through which an axial aperture extends, said aperture having a front end into which the rear end of the barrel is received, and (ii) a pair of opposed finger grips that are elongated to each accommodate two fingers said finger grips extending outwardly from the central body.

BRIEF DESCRIPTION OF THE DRAWINGS

In the drawings, which are not to scale:

FIG. 1 is a perspective view of an embodiment of the syringe of the invention being held in the hand;

FIG. 2 is a schematic front elevational view comparing the syringe of FIG. 1 to the ANGIOJECT syringe (one-half of the syringe of FIG. 1 is shown to the left of the centerline, and one-half of the ANGIOJECT syringe is shown to the right of the centerline);

FIG. 3 is a elevational, partly sectional view of the syringe of FIG. 1;

DETAILED DESCRIPTION OF THE INVENTION

Figure 4:
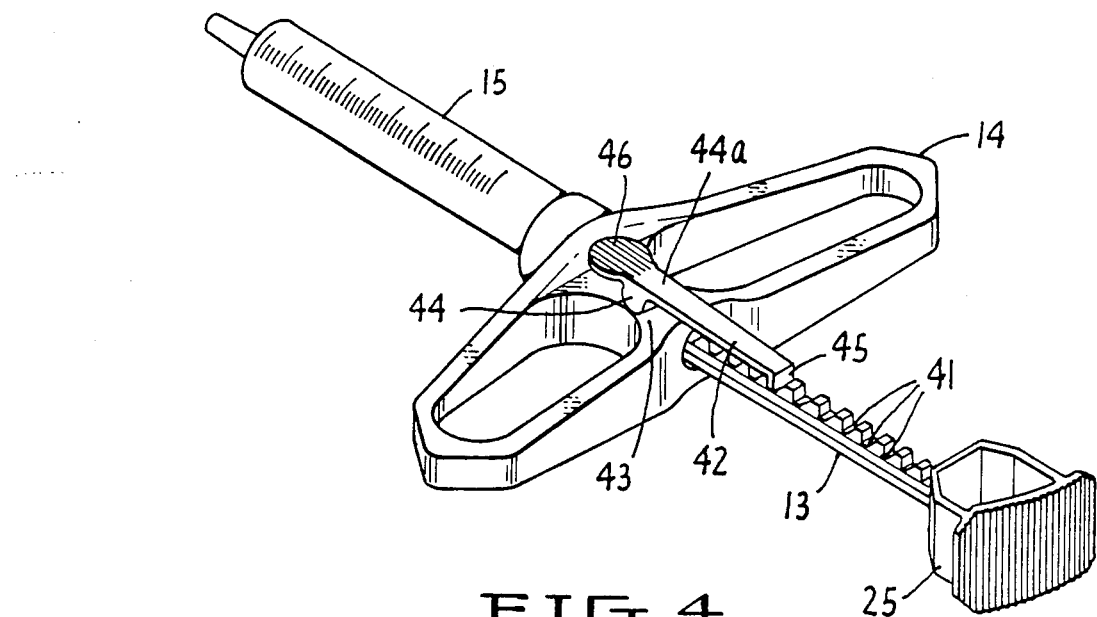
FIG. 4 is a perspective view of another embodiment of the invention that includes means for locking the plunger of the syringe.

FIGS. 1 and 3 depict the preferred embodiment of the syringe of the invention, generally designated 11. Syringe 11 basically has three components: a cylindrical barrel 12, a plunger 13, and a handle 14.

The lumen 15 of barrel 12 is adapted to hold the fluid to be injected (when the plunger is extended or retracted). The front end 16 of the barrel terminates in a small diameter nozzle 17 and has a luer-lock fitting 18 which may be used to connect the barrel to extension tubing, catheter fittings, and the like.

Plunger 13 consists of a shaft 19 whose front end 22 carries a cylindrical piston member 23 that fits snugly and sealinqly within lumen 15 and is adapted to drive the fluid from the lumen during operation of the syringe. The shaft may be splined to increase its column strength and decrease its volume (and hence weight). The rear end 24 of the shaft carries a ring-shaped head 25 that has a serrated crown 26 that is adapted to fit within the palm of the hand (FIG. 1). The ring-shaped head provides a finger/thumb grip for retracting the plunger and a thumb grip in the event it is desired to plunge the plunger with force exerted by the thumb rather than the palm.

Handle 14 comprises a central body portion 27 that has an axial bore 28 extending therethrough and a pair of opposed finger grips 29, 32. Bore 28 has a front section 33 of sufficient diameter to accommodate barrel 12. As seen in FIG. 3, the rear end of the barrel carries a collar or flange 34 that is seated in a radial channel 35 in body portion 27. Bore 28 has a rear section 36 of smaller diameter than front section 33 but sufficient to receive the plunger shaft therethrough. The rear section of bore 28 opens into a recess 30 in the rear surface of the handle that is configured so that the base of head 25 can nest therein when the plunger is depressed. Such configuration permits a further lessening of the distance between the fingers and the crown of the head when the plunger is extended. Finger grips 29, 32 are in the shape of slotted or apertured wings that are angled or inclined rearwardly. The apertures 37, 38 in grips 29, 32 are oval shaped to accommodate a comfortable grip of the handle by the second, third, fourth and fifth fingers.

FIG. 2 illustrates the advantages of syringe 11 relative to the ANGIOJECT syringe. The principal differences in the two syringes are:

(1) In syringe 11 the finger grips are located rearwardly of the barrel, and are angled rearwardly relative to the barrel. Also the base of the head of the plunger nests in the recess of the rear surface of the handle when the plunger is depressed. These differences make the distance (designated "a" in FIG. 2) between the grips and the top surface of crown 26 shorter in the invention syringe than in the ANGIOJECT syringe. In quantitative terms, the distance is approximately 4.45 inches in the ANGIOJECT syringe, whereas it is only approximately 3.75 inches in the proposed commercial embodiment of the invention syringe. The invention syringe can thus be gripped comfortably in the hand with the fingers inserted into the grip apertures and the crown of the fully extended plunger resting against the palm (as in FIG. 2).

(2) The finger grips in syringe 11 are positioned laterally of the plunger shaft, whereas in the ANGIOJECT syringe the grips are positioned laterally of the rear section of the barrel. In this regard, since the diameter of the barrel is greater than the diameter of the plunger shaft, the space (designated "b" in FIG. 3) between the inner ends of the grips (and thus the distance between the third and fourth fingers) may be made smaller in the invention syringe than in the ANGIOJECT syringe. Keeping that space small enables the user to grip the handle more strongly. In quantitative terms, this space in the ANGIOJECT syringe is approximately 0.332 inches, whereas in the proposed commercial embodiment of the invention device it is only about 0.290 inches.

Another advantage of the invention device over the ANGIOJECT device is that the seating of the barrel end in the handle aperture may be altered (such as by threading the aperture and end) in the invention device so as to make the barrel removable so that it may be replaced with other barrels of different volume. It is also easier to view the contents of the barrel in the embodiment since they are not as obscured by the handle. Still another advantage is that the aperture of the finger grips of the invention syringe are enclosed, thus making the invention syringe easier to store by hanging. Yet another advantage is that the crown of the invention syringe's plunger is serrated whereas the crown of the ANGIOJECT syringe is smooth. This makes the invention syringe more slip-resistant.

FIG. 4 illustrates a variation of the syringe of FIG. 1 that is essentially identical to the syringe except that it includes means for reversibly locking the plunger at a given predetermined position. Those means comprise a series of spaced notches 41 in the shaft 19 of the plunger and a locking tang, generally designated 42. The tang is affixed to the flat surface 43 of the handle at a fulcrum point 44 between the finger grip openings. The tang comprises an elongated axially extending body 44 one end of which carries a tooth 45 that is adapted to fit into the notches 41 and the other end of which is a head 46 that serves as a point for depressing said other end. In operation, the tang operates as a lever with the tooth of the tang being disengaged by exerting finger pressure on head 46 to lever the other end of the body up and away from the notched shaft.

Figure 5:
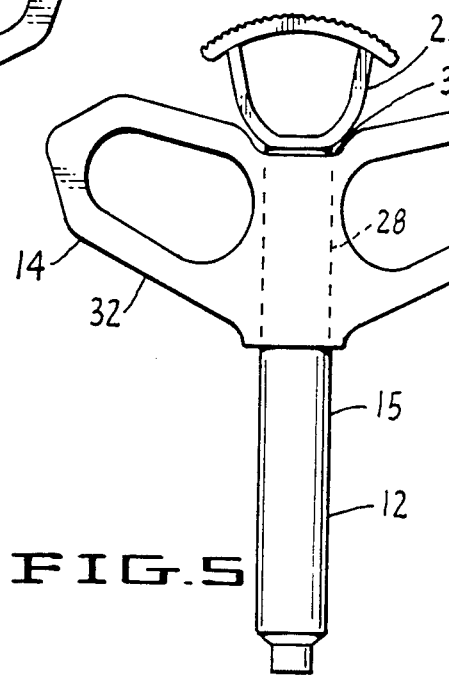
FIG. 5 is a front elevational view of yet another embodiment of the invention.

FIG. 5 depicts a variation of the syringe of FIG. 1 in which the barrel 12 extends entirely through bore 28 rather than only through a front section of the bore as in FIG. 1. Otherwise, the syringe of FIG. 6 includes the distinctive features of the syringe of FIG. 1, namely the rearwardly angled elongated finger grips and the nesting of the base of head 25 in recess 30 in the rear surface of handle 14. As indicated above such nesting and angling of the finger grips diminish the distance between the finger grips and the crown when the plunger is extended.

Figure 6:
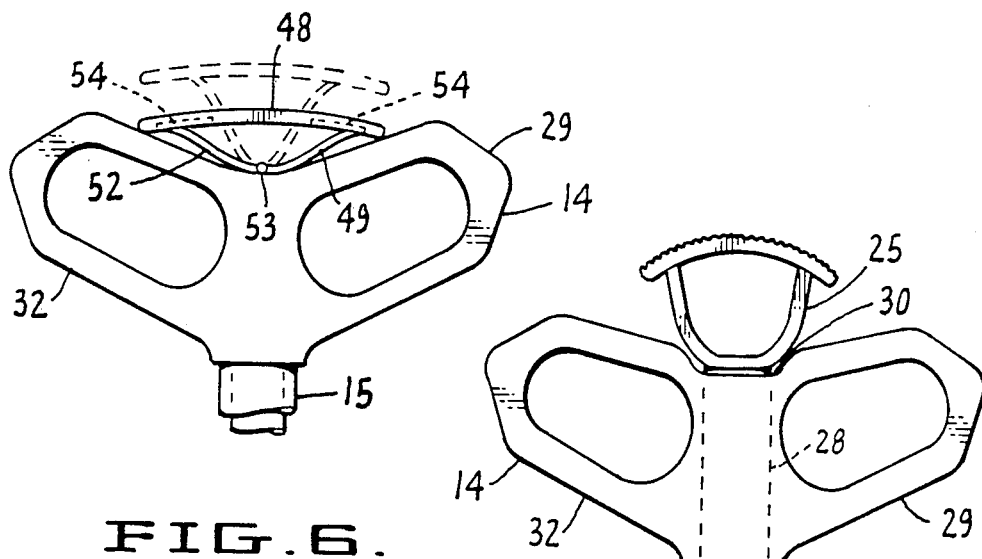
FIG. 6 is a partial schematic front elevational view of another embodiment of the invention in which the head of the plunger is collapsible.

FIG. 6 illustrates another variation in the syringe of FIG. 1 in which the distance between the finger grips and the crown of the plunger head is shortened by making the plunger head collapsible such that its axial dimension is diminished. In FIG. 6 the collapsed configuration of the head is shown in solid line, whereas the normal (uncollapsed) configuration is shown in phantom. The collapsible head comprises a crown 48 and a base composed of two legs 49, 52. The forward ends of legs 49 and 52 are commonly pinned at 53 such that they are free to rotate about point 53. Preferably these ends are spring backed so that the legs are biased to an upright position (shown in phantom). The front surface of the crown 48 has a pair of slots 54 in which the rear ends of the legs are permitted to slide. With such structure the head collapses when forward axial pressure is placed on the crown. When that pressure is released the legs spring back to their upright position to provide the head with an enclosed aperture that serves as a thumb grip for manipulating the plunger. It will be appreciated that other means, such as hinged legs or deformable, resilient legs may be used instead of the structure shown in FIG. 6 to permit the head to collapse.

Modifications of the above-described embodiment of the syringe that are obvious to those of skill in the syringe and medical device arts are intended to be within the scope of the following claims.

We claim:

1. A manually driven syringe comprising:
   (a) a barrel for housing a fluid to be injected having a front end having a fluid outlet and a rear end;
   (b) a plunger comprising a shaft that is received within the barrel and ha a front end which carries a piston and a rear end which carries a head that is adapted to fit within the palm of the hand said head having a front surface and a rear surface; and
   (c) a handle member having
      (i) a central body having ga front surface and a rear surface through which an axial aperture extends, said aperture having a front end into which the rear end of the barrel is received, and
      (ii) a pair of opposed wing-shaped finger grips each of which defines an enclosed opening elongated to accommodate two fingers that extends outwardly from the central body of the rear section and is angled rearwardly relative thereto so as to define a line of grip for said two fingers that is angled rearwardly relative to the axis of the body whereby the distance between the location on the grips where the second, third, fourth and fifth fingers are placed and the plunger head when the plunger is extended is lessened.

2. The syringe of claim 1 wherein the aperture has a front section into which the rear end of the barrel extends and a rear section of smaller diameter than the front section and through which the shaft of the plunger extends and the finger grips extend laterally of the rear section of the aperture with the distance between the inner ends of the finger grips being less than the diameter of the barrel.

3. The syringe of claim 2 wherein the rear end of the aperture opens into a recess in the rear surface of the body and the front surface of the head of the plunger is configured to nest within the recess abutting the rear surface of the body when the plunger is fully depressed.

4. The syringe of claim 3 wherein the head is serrated whereby the likelihood of the head slipping in the palm of the hand is lessened.

5. The syringe of claim 3 wherein the barrel is removably seated in the front section of said aperture whereby the barrel may be removed and replaced with another barrel of different fluid volume.

6. The syringe of claim 2 wherein the head is ring-shaped and collapsible under axial pressure from an uncollapsed configuration in which the head forms an enclosed opening that provides a thumb grip to a collapsed configuration in which the axial dimension of the head is diminished.

7. The syringe of claim 2 including means for reversibly locking the plunger in a predetermined position comprising a series of spaced notches in the plunger shaft and a locking tang attached to the handle and having a tooth that is adapted to engage said notches.

8. A manually driven syringe comprising:

(a) a barrel for housing a fluid to be injected having a front end having a fluid outlet and a rear end;

(b) a plunger comprising a shaft that is received in the barrel and has a front end which carries a piston and a rear end which carries a ring-shaped head that is adapted to fit within the palm of the hand, said head being collapsible under axial pressure from an uncollapsed configuration in which the head forms an enclosed opening that provides a thumb grip to a collapsed configuration in which the axial dimension of the head is diminished; and (c) a handle member having
  (i) a central body through which an axial aperture extends, said aperture having a front end into which the rear end of the barrel is received, and
  (ii) a pair of opposed finger grips that are elongated to each accommodate two fingers said finger grips extending outwardly from the central body.

* * * * *